(12) United States Patent
Gu et al.

(10) Patent No.: US 7,780,761 B2
(45) Date of Patent: Aug. 24, 2010

(54) ADSORPTIVE GAS SAMPLER USING IONIC NANO-DROPLETS

(75) Inventors: Alex Gu, Plymouth, MN (US); Wei Yang, Minnetonka, MN (US); Matthew S. Marcus, Plymouth, MN (US); Adam Dewey McBrady, Minneapolis, MN (US)

(73) Assignee: Honeywell International Inc., Morristown, NJ (US)

( * ) Notice: Subject to any disclaimer, the term of this patent is extended or adjusted under 35 U.S.C. 154(b) by 346 days.

(21) Appl. No.: 11/935,955

(22) Filed: Nov. 6, 2007

(65) Prior Publication Data

US 2009/0114090 A1    May 7, 2009

(51) Int. Cl.
  *B03C 3/014* (2006.01)
(52) U.S. Cl. ............ 95/66; 95/67; 95/71; 95/73; 96/27; 96/53; 96/55; 96/59
(58) Field of Classification Search .......... 95/65–67, 95/71, 73; 96/27, 53, 55, 59; 239/690, 697, 239/698
  See application file for complete search history.

(56) References Cited

U.S. PATENT DOCUMENTS

| | | | | |
|---|---|---|---|---|
| 3,503,704 A | * | 3/1970 | Marks | 423/212 |
| 3,785,124 A | * | 1/1974 | Gaylord | 96/19 |
| 3,800,505 A | * | 4/1974 | Tarves, Jr. | 95/66 |
| 4,095,962 A | | 6/1978 | Richards | |
| 4,146,371 A | * | 3/1979 | Melcher et al. | 95/62 |
| 4,193,774 A | * | 3/1980 | Pilat | 95/71 |
| 4,305,909 A | * | 12/1981 | Willett et al. | 422/169 |
| 5,000,762 A | * | 3/1991 | Lindquist et al. | 95/66 |
| 5,282,885 A | * | 2/1994 | Cameron | 95/66 |
| 5,518,525 A | * | 5/1996 | Steed | 95/58 |
| 5,714,126 A | * | 2/1998 | Frund | 422/122 |
| 5,902,380 A | * | 5/1999 | Tomimatsu et al. | 96/27 |
| 5,968,231 A | * | 10/1999 | Parmentier et al. | 95/28 |
| 6,110,256 A | * | 8/2000 | Reynolds et al. | 95/4 |
| 6,156,098 A | | 12/2000 | Richards | |
| 6,193,782 B1 | * | 2/2001 | Ray | 95/4 |
| 6,235,088 B1 | * | 5/2001 | Matsuura | 96/53 |

(Continued)

FOREIGN PATENT DOCUMENTS

GB     2019746 A  * 11/1979  ............... 96/53

OTHER PUBLICATIONS

Kato, Ryo, et al., "Systems with ionic liquids: Measurement of VLE and cl data and prediction of their thermodynamic behavior using original UNIFAC, mod. UNIFAC(Do) and COSMO-RS(OI)", *J. Chem. Thermodynamics*, 37, (2005),603Ā?619.

(Continued)

*Primary Examiner*—Richard L Chiesa
(74) *Attorney, Agent, or Firm*—Schwegman, Lundberg, & Woessner P.A.

(57) ABSTRACT

A gas sampling canister has an electrospray nozzle for creating an ionic fluid electrospray plume. A gas sample intake is positioned to provide a gas sample flowing through the ionic fluid electrospray plume. A cooled counter electrode is positioned to collect the electrospray plume such that selected chemicals in the gas sample are captured by ionic fluid accumulating on the cooled counter electrode. A system and method for sampling gas are also described.

19 Claims, 5 Drawing Sheets

U.S. PATENT DOCUMENTS

| | | | |
|---|---|---|---|
| 6,471,753 B1 * | 10/2002 | Ahn et al. | 96/27 |
| 6,508,861 B1 * | 1/2003 | Ray | 95/79 |
| 6,824,587 B2 * | 11/2004 | Mohamed | 95/7 |
| 6,860,434 B2 * | 3/2005 | Ahn et al. | 239/102.1 |
| 6,986,803 B1 | 1/2006 | Richards | |
| 2003/0056648 A1 * | 3/2003 | Fornai et al. | 95/65 |
| 2004/0023411 A1 * | 2/2004 | Fenn | 436/174 |
| 2004/0089156 A1 * | 5/2004 | Gartstein et al. | 96/53 |
| 2006/0185511 A1 | 8/2006 | Tepper | |
| 2006/0191413 A1 * | 8/2006 | Weidmann | 96/44 |
| 2008/0063558 A1 * | 3/2008 | Coleman | 422/4 |
| 2008/0121106 A1 * | 5/2008 | Tepper et al. | 96/27 |
| 2009/0235817 A1 * | 9/2009 | Gu et al. | 95/79 |

OTHER PUBLICATIONS

Martinez-Sanchez, Manuel, "Lecture 23-25: Colloidal Engines", *16.522, Space Propulsion*, (No date listed),1-36.

* cited by examiner

ADSORPTIVE GAS SAMPLER USING IONIC NANO-DROPLETS

BACKGROUND

Existing air sampling technologies have major limitations. Summa canisters have been the gold standard for air sampling technologies. A Summa canister is a stainless steel vessel which has had the internal surfaces specially passivated using a "Summa" process. This process combines an electropolishing step with chemical deactivation to produce a surface that is chemically inert. A Summa surface has the appearance of a mirror, bright and shiny. In some cases, an additional adsorption layer is added to the surface of the summa canister. When combined with subsequent gas chromatography-mass spectrometry (GC-MS) analysis, they yield the most accurate data of all commercially available technologies. The cost, size, weight, and labor intensive handling of Summa canisters, however, make them unattractive for chemical reconnaissance. In terms of cost and size, solid-absorbent sampling tubes and solid phase micro-extraction (SPME) sampling technologies would be more suitable, but these technologies show large discrepancies when compared to Summa canister data. These discrepancies are due in large part to the comparatively narrow adsorption spectrum and selective gas adsorption of the solid absorbents and the limited absorption capabilities of the polymeric coatings on the SPME fiber.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

An ionic liquid electrospray with a cooled counter electrode is used to collect polar and polarizable molecules. Various embodiments are described that utilize the electrospray in combination with solid absorbents in a cartridge or canister form that can also be used with a system to remove water from a gas such as air, and move the air through the cartridge. Multiple cartridges may be used in a sampling system, and in some embodiments, each cartridge may be sealed after used for sampling air, and sent to be analyzed in a laboratory. In some embodiments, in combination with superb non-polar compound capturing capability of existing solid absorbent, charged nanodroplet enhanced sampling may be used to capture organics, acids, halogens, noble gases, and organometallics with a dynamic range from 10 ppt to 100 ppm with sufficient quantity for subsequent GC-MS analysis. The cartridge may be a highly miniaturized sampling capsule (<3 ml in volume). The sampling capsules utilize the ionic liquid electrospray to pre-concentrate, dissolve, and preserve polar and polarizable gases. The sampling capsules may also utilize layered solid absorbents to capture low polarizability non-polar gases and a void space to contain noble gases as well as other gases that do not interact with the ionic liquid or solid phase materials.

Figure 1:
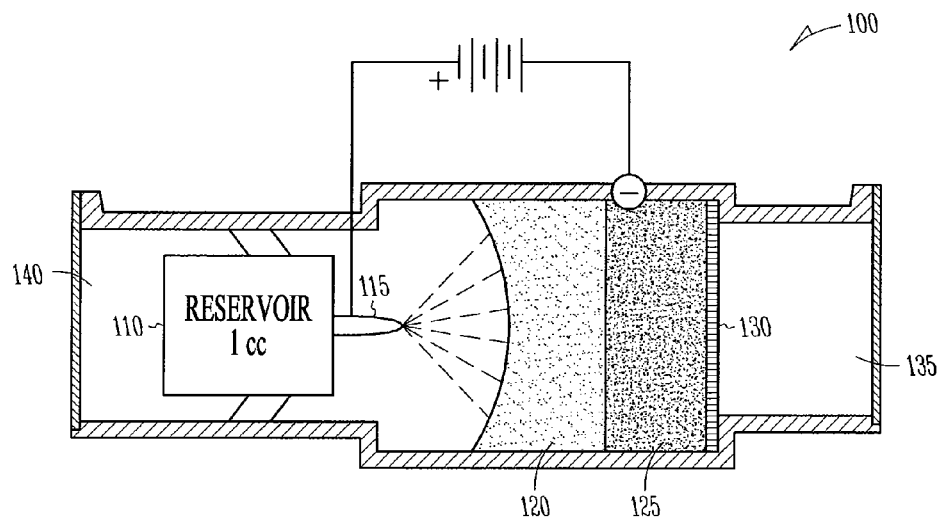
FIG. 1 is a block cross section representation of a gas sampling canister according to an example embodiment.

FIG. 1 is a block cross section representation of a gas sampling canister 100 according to an example embodiment. The canister may include a wall 105 formed of stainless steel, plastic or other material compatible with materials within the wall of the canister 100. In one embodiment, the wall is cylindrical in shape in one embodiment. Within the wall of the canister, is an ionic liquid reservoir 110, an electrospray nozzle 115 coupled to the reservoir 110, and a cooled counter electrode 120. A solid phase adsorption material 125 is disposed adjacent the counter electrode 120, followed by a frit, such as a metal screen 130 to contain the material 125 within the canister 100. Plates 135 and 140 are disposed on both ends of the canister 100, and may seal the canister prior to use to avoid contamination. The plates 135, 140 are moveable to expose the internal elements of the canister to gas, and to re-seal the canister after exposure to gas for a desired amount of time. Re-sealing prevents loss of analyte and also prevents contamination.

In one embodiment, canister 100 is an open tubular structure with flanges at both ends. As manufactured, the ends may be covered by metallized polymer films adhesively bonded to the flanges. The film extends over one side of the end of the flange and is bonded to a small diameter shaft. The seal is opened by turning the shaft, breaking the adhesive seal and tightly rolling up the polymer film onto the shaft. The two ends of the capsule can be opened synchronously providing openings for drawing air samples through the capsule.

Resealing the capsule after exposure is equally simple, assuming that suitable sealing films and adhesives can be found. Ideally the original sealing film can be reused by unrolling the rolled-up film back onto the flanged surfaces of the capsule. Axial pressure would be applied to the two ends to insure the integrity of the adhesive seal. The upstream end of a canister would be closed first, establishing a vacuum (a few psi) in the canister that would aid the sealing process. If tight seals cannot be achieved in this way, fresh polymer films with fresh adhesives can be used with minor complication of the robotic actuator system.

In one embodiment, an inner side of wall 105 of the canister 100 may be passivated using a "Summa" process, such as the same one used in Summa® canister construction, before loading other components into the canister. This process combines an electropolishing step with chemical deactivation to produce a surface that is chemically inert. The canister may be pre-heated right before sampling to desorb any "left-over" gases adsorbed during storage.

In addition to the sampling canister treatment, tubing in the gas path may be passivated to avoid adsorption of analytes.

Swagelock manufactures and sells deactivated stainless steel tubing for the analytical production of trace gas standards.

Figure 2:
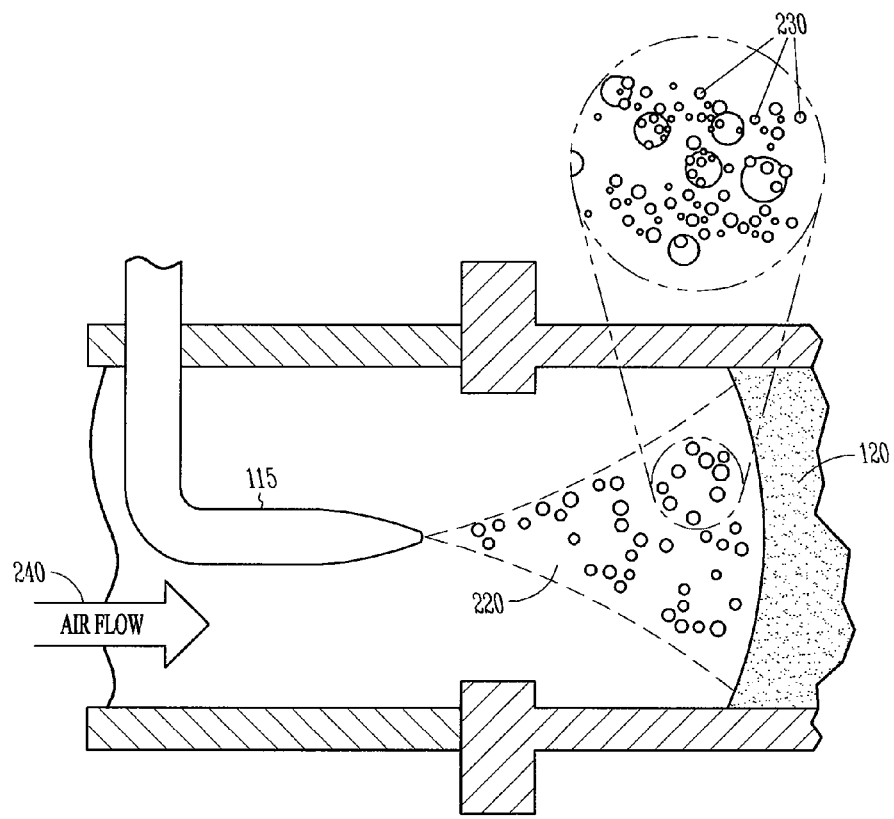
FIG. 2 is a block diagram illustrating details of a gas sampling ionic electrospray according to an example embodiment.
Figure 3:
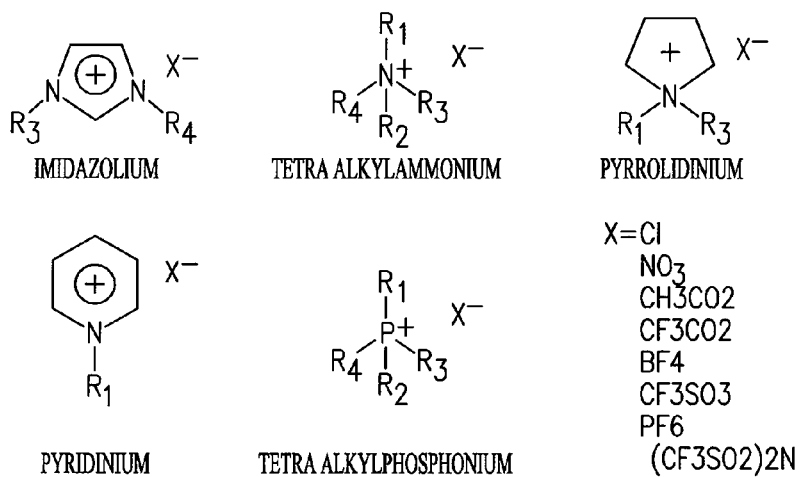
FIG. 3 illustrates some example ionic compounds that may be used in an electrospray gas sampling system according to an example embodiment.
Figure 4:
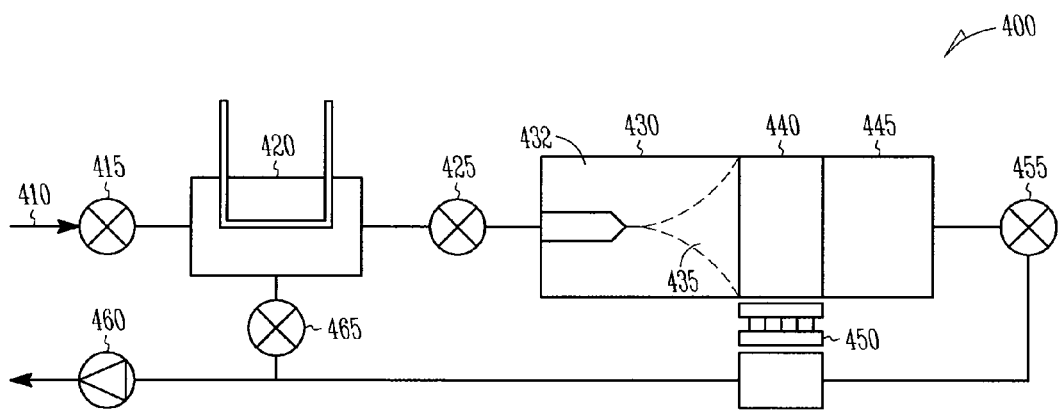
FIG. 4 is a block schematic representation of system for sampling gas according to an example embodiment.
Figure 5:
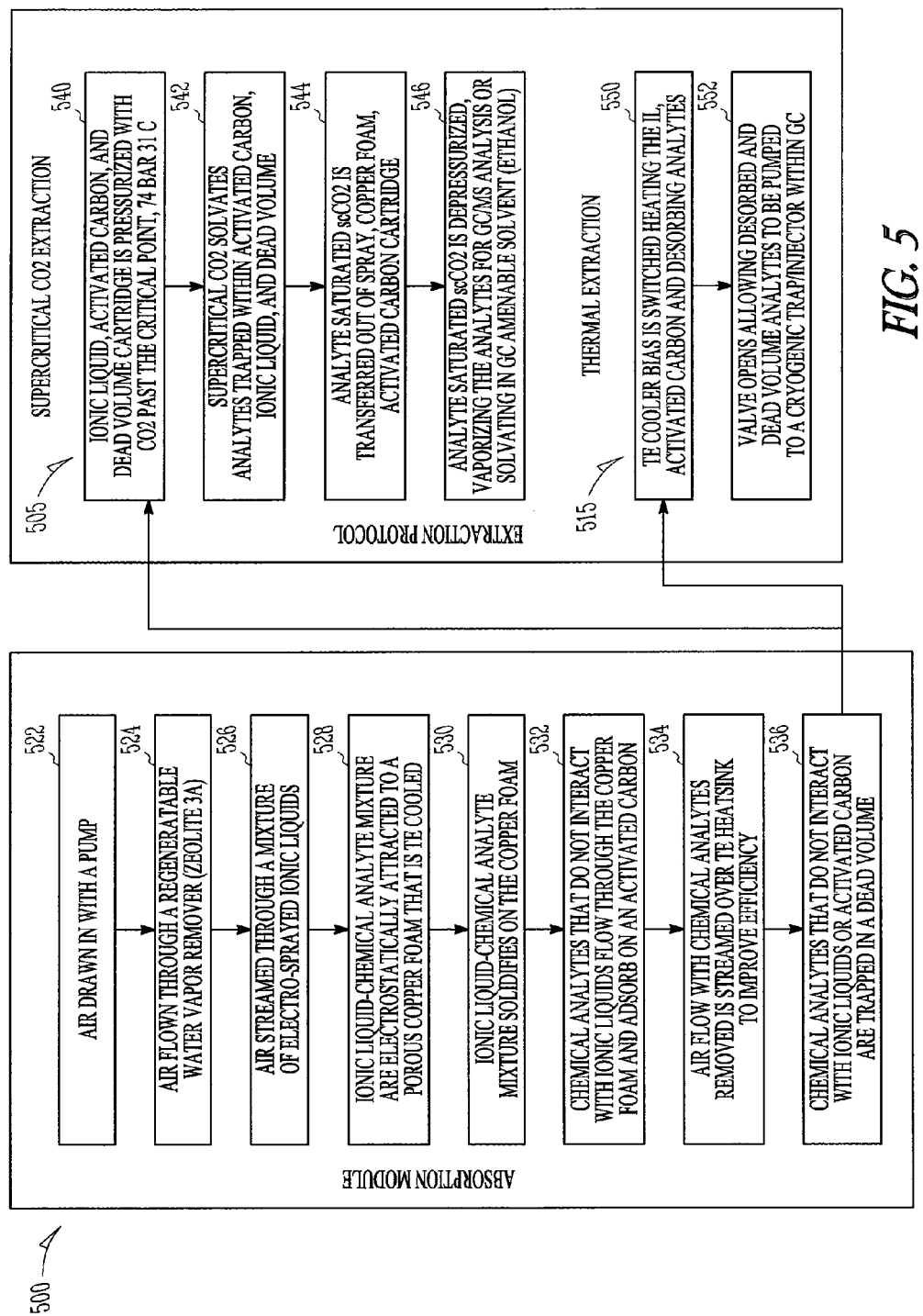
FIG. 5 is a block flow diagram of a process for sampling gas according to an example embodiment.

FIG. 2 is a cross section representation of an electrospray method of capturing analytes (gas molecules). A voltage 210 is applied between the nozzle 115 and counter electrode 120. In one embodiment, the counter electrode 120 is a copper foam. An electrospray plume 220 of the ionic fluid is represented in FIG. 2. The plume 220 contains a large number of ionic liquid nano-droplets, forming a high surface area structure. The high surface area of the spray plume increases the interaction probability between gases and the ionic liquid, ensuring high capture efficiency.

In one embodiment, a gas stream is directed through the canister. Gas that interacts with the nano-droplets in the spray plume is captured by dissolving into the ionic liquid forming a nanodroplet-analyte combination, sometimes simply referred to as an analyte. Nano droplets of the ionic fluid are represented by round particles. A gas 240 to be sampled contains chemical represented by circles 230 in the inset. The chemicals pass through the spray plume 220 and are coated with the nanoparticles. The nanoparticles are then electrostatically attracted to the counter electrode 120, which is cooled. The cooled electrode causes the ionic liquid to transition into a glassy state, effectively trapping the analyte.

In one embodiment, the counter electrode 120 is thermoelectrically cooled to approximately 250° K. Different ionic fluids may provide desired results at different temperatures of the counter electrode 120. Other methods of cooling the electrode 120 may be used, such as the use of a refrigerant or other mechanism. The cooled electrode causes the ionic liquid spray to transition into a glassy state, effectively trapping the analytes. In one embodiment, the electrode may be designed to ensure that the pores will not clog as the analyte accumulates. The small amounts of analytes that aren't captured by the ionic liquid, such as light hydrocarbons, remain in the air stream, and are drawn through a solid phase adsorbing material, such as nanostructured activated carbon. Solid phase adsorbents are well known for their capability in capturing light hydrocarbon gases, ensuring high sampling efficiency.

As a final step, the capsule is resealed trapping a small volume (~1 cc—depending on the size of the canister) of air which will enable sampling of gases that are above the parts-per-billion level. Pertinent gases, such as krypton and xenon, which have background levels above the 10 ppb level will be trapped in this "dead volume" as well as being weakly adsorbed by the ionic liquid.

Electrosprayed ionic liquids will sample all polar and polarizable gas molecules in an air stream passed through sprayed nano-droplets. The nano-droplets provide a greatly increased surface area of the ionic liquid, increasing the number of molecules attaching to the spray. The use of electrosprayed ionic liquids provides the ability to pre-concentrate, dissolve, and preserve all polar gases. It may be used in combination with layered solid absorbents to capture low polarizability non-polar gases and a void space in the canister to contain noble gases.

In one embodiment, solid phase adsorptive material 125 may be a combination of loosely packed micro- or nano-powders whose surface structures and chemistries collectively bind many classes of molecules firmly but reversibly. Mixtures of Zeolites and other adsorbents, with various pore sizes, may be used to trap a wide range of analytes. For example, a hydrophobic adsorbent like a nanoporous carbon or high silica Zeolite may be used along or may be paired with a more hydrophilic adsorbent to maximize the variety of adsorbents to be collected. In one embodiment, Zeolite, activated carbon, and silica gels, may be used with pores of approximately 8-15 Angstroms. Such a pore size will work for a wide range of molecules, since the great majority of analytes will enter the pores.

The canister 100 is designed to capture lighter hydrocarbons, halogens and other less polar gases that are not effectively captured by electrospray ionic liquids. The solid adsorbent 125 may serve a scavenging role, intercepting traces of more polar analytes which may, for whatever reason, have bypassed the electrospray system. The solid adsorbent is adjacent to the cooled copper foam, so adsorption of analytes will be enhanced. Light hydrocarbons have significant vapor pressure, even at the lower temperatures expected, and it is expected that their background concentrations will be significantly higher than 10 ppt.

Adsorbents in various embodiments may include hydrophobic inorganic materials like silicalite, nanoporous carbons, activated carbons, and Zeolite. These materials combine high micropore surface area (>800 m2/g for pores 10-15 Å in diameter), with efficient mesopore channel networks for acceptable uptake rates. Commercially available solid phase adsorbents comprising a support coated with an organic coating including long alkyl sidechains may also be of interest. Though lower in surface area, these materials are particularly effective for adsorption of hydrocarbons. If required multiple adsorbents can be combined to provide optimum sorption.

The format of the solid adsorbents may be selected to ensuring efficient sampling of the passing air stream. Low pressure drop is desired, but bypass should be avoided. In one embodiment, a structured format, either as coatings on a corrugated support or in a monolith may be utilized based on anticipated flow characteristics of the gas stream through canister 100.

The use of the ionic electrospray in place of additional solid phase adsorbents helps overcome a problem referred to as competitive displacement. The majority of gases have very similar solid phase absorption mechanisms. This similarity is useful in enabling exhaustive sampling of all possible atmospheric compounds. Understanding this mechanism sheds light on the difficulties solid phase absorbers face in meeting the first two challenges. Generally, gas adsorption starts with physisorption. For instance, Zeolite and other high surface area adsorbents function by adsorbing analytes first as a physisorption process, and subsequently as a pore-filling condensation process as the physisorption sites get filled.

When only trace amounts of gas are present, the gases form a physisorbed monolayer on the Zeolite surface. During this phase, interactions between the analyte and the adsorbent surface will dominate. As the total gas concentration increases, the pores of the absorber begin filling at which time the adsorbed gas will form an adsorbed liquid-like phase. The driving force will now be the interactions between the analyte and this incipient phase. The efficiency of adsorption depends on the concentration of the analyte in the air. At low concentrations on a virgin adsorbent, the adsorption affinity will be high but the capacity will be low (being restricted to a monolayer). As the quantity of adsorbate on the adsorbent increases, the average strength of each interaction will decrease. When various analytes are present in the sampled air, each analyte competes for adsorption sites. A large concentration of analyte will dominate the strong monolayer interactions leaving the low concentration analyte to have weaker interaction with the insipid layer. The problem is exacerbated if the high concentration analyte-absorbent interaction is energetically preferred. This solid absorbent phenomena of high concentration analytes prevents other analytes from adsorbing and is referred to as competitive displacement.

Ionic liquid materials offer many advantages for gas capture, including wide range of solubilities and thermal and electrical stability. Many different ionic liquids materials may be used. In one embodiment, 1-butyl-3-methylimidazolium tetrafluoroborate or [bmim][BF4] is used.

Electrospraying any liquid produces an incredible high surface area mist. The ultra-fine charged droplet mist results from applying a high voltage (several kVs/cm) between a small (100 s of micrometers) electrospray nozzle and a counter electrode. Typical droplet generation rates are on the order of $10^{10}$ of these droplets are generated per second at 17.5 μl/min spray rate. The droplets in the mist are highly charged, often carrying in excess of 2,000 Coulomb per kilogram. The incredible charge density separates individual droplets in the mist plume. Typical droplet size ranges are from 100 s of nm to ionic emission (sub-nm). The flow rate may have an effect on resulting droplet size and therefore plume surface area. Depending on the selected ionic liquid mixture and resulting flow rate, we can expect droplet between 3.16 to 89.4 nm and surface areas between 678 and 24 $m^2$/g. High surface area and small droplet size are beneficial for effective gas adsorption and dissolution. From the above numbers and our canister size, the typical diffusion time of gases from to the surface of a droplet is approximately 27 μsec. Subsequent dissolution of the surface-adsorbed gases into the droplet take approximately 0.1 μsec. The mean resident time of a droplet inside the canister is ~5 msec, or ~200-times longer than the time needed for gas adsorption and dissolution. Stated simply, the electrospray process solves the resistance to mass transfer seen in bulk ionic liquids.

The sweeping volume of the nanodroplets is orders of magnitude higher than the gas volume. Sweeping volume is defined as the total volume sampled by the charged droplet before they reach the counter electrode. Sweeping volume is defined by:

$$V_s = N \times A_d \times V_{gd}$$

where Vs is the nanodroplet sweeping volume in L/s, N is the number density of nanodroplets per second, A is the droplet cross sectional area, and $v_{gd}$ is the relative velocity between the gas stream and the nanodroplets in m/s. For a 17.5 μl/min electrospray, around 10 billion 89 nm nanodroplets are generated per second. Assuming gas/droplet relative velocity of 2 cm/s, the nanodroplets sweeping volume is 300× greater than the gas volume they sample (gas volumetric flow is around 15 ml/s in one embodiment). Such a large sweeping volume ensures complete sampling of entire gas volume by the droplets. The sweeping effect exits for all spray-based air scrubbing technology regardless if the droplets are charged or not. The increase in sweeping volume becomes larger when the droplet sizes are relatively large (>1 μm).

Strong mutually induced dipole-dipole interaction occurs between charged droplet and polar gas molecules. The electrosprayed nanodroplets obtain very high charge-to-mass ratios, often exceeding 2,000 coulomb/kg. They essentially behave like "quasi" mobile ions. When the droplets encounter polar or polarizable gas molecules, both the charged nanodroplets and the polarized gas molecules attract each other. This attraction increases the gas concentration in the microenvironment around the charged droplet. This effect becomes more prominent as the droplet size approaches that of an individual gas molecule, and especially when the gas concentration is at sub-ppm level.

In one embodiment, the counter electrode exhibits good thermal and electrical conductivity. The foam should also allow the gas sample to pass through it with the lowest possible pneumatic pressure drop at complete NAC capturing efficiency. Copper foam, with appropriate pore size, represents an ideal candidate. Copper has very good thermal and electrical properties with a customizable pore size. Larger pore size will decrease the pneumatic pressure drop, while smaller pore sizes favor NAC capturing. In one embodiment, a counter electrode formed of copper foam provides less than an 8 psi pneumatic pressure drop, and an analyte foam residence time greater than the analyte pore wall collision time. In one embodiment, a 1-cm cylindrical copper foam with 1 $cm^2$ cross sectional area is used. The following Table 1 summarizes the trade offs of the pore size for optimal copper foam configuration. As can be seen, copper foam with pore size ranging from 100 to 200 μm offers low pressure drop, good droplet capturing efficiency, and rapid cooling/gelation of the captured droplets (~29 ns).

TABLE 1

| Copper foam Pore size (um) | Pneumatic pressure drop (Pa) | Droplet colliding time (msec) | Cooling time for ΔT = 70° C. (ns) | Droplet resident time in the pore (msec) |
|---|---|---|---|---|
| 50 | | 1.25 | 29.1 | 5 |
| 100 | | 2.5 | | |
| 200 | | 5 | | |
| 400 | | 10 | | |

Assuming 2-cm long straight pores with 90% porosity (0.89 g); 4 m/s and 2 cm/sec for gas and droplet velocities; 50 nm ionic liquid droplet with thermal diffusivity of 8.60E−4 $cm^2$/s.

Electrospray of ionic liquid into the canister module seamlessly integrates effective trace compounds adsorption offered by highly charged nanodroplets; rapid dissolution of the absorbed compounds into ionic liquid droplets; and effective preservation of captured trace compounds through solidification/gelation of ionic liquid. It may provide complete and exhaustive polar and polarizable analyte capturing, and easy analyte preservation.

FIG. 4 is a block schematic representation of a system 400 for sampling gas according to an example embodiment. System 400 receives gas at 410 via a first valve 415. The elements of system 400 will be described in the same sequence as the flow of air to be sampled. A water remover 420 removes most water from the gas sample. It is desired to capture most if not all gases other than $O_2$, $N_2$ and $H_2O$. A second valve 425 allows access of the water depleted air to a sampling canister 430, which may be similar in construction to canister 100, or of other design. The canister 430 contains a dead space 432 for sampling noble and other gases, and also combines ionic fluid nanospray 435 with counter electrode 440 and solid adsorbents 445. A cooler 450 is used to cool the counter electrode 440. A third valve 455 is used in conjunction with the second valve 425 to seal and unseal the canister 430 such that only a desired stream of gas is sampled. In one embodiment, the gas flows through the canister and is routed past the cooler 450, which may have heat fins for conducting heat away from the cooler. The gas is then ejected via a pump 460. A fourth valve 465 is positioned between the water remover and the pump 460 to divert gas flow for ejection when the canister is sealed and not sampling gas.

FIG. 5 is a block flow diagram of a process 500 for sampling gas, a supercritical $CO_2$ extraction process 505, and a thermal extraction process 515 according to an example embodiment. In sampling process 500, which may utilize system 400, a gas sample, such as air is drawn into the system 400 with a pump at 522. The air is then flown or passed through a regeneratable water vapor remover 524, such as Zeolite 3A. The air is then streamed through a mixture of electrosprayed ionic liquids at 526 for about 4 minutes in one embodiment before valves are closed to seal the canister. At 528, a resulting ionic liquid-chemical analyte mixture is electrostatically attracted to a counter electrode, such as a porous copper foam that is cooled. In one embodiment, a temperature differential of approximately 70° C. is created between the dead space and the counter electrode. The mixture solidifies on the copper foam at 530. At 532, chemical analytes that do not interact with ionic liquids flow through the copper foam and adsorb on a solid adsorbent, such as activated carbon. Air flow with chemical analytes removed is streamed over a heat sink of the cooler at 534 to improve efficiency in one embodiment. Chemical analytes that do not interact with ionic liquids or activated carbon are trapped in the dead volume 536.

Figure 6:
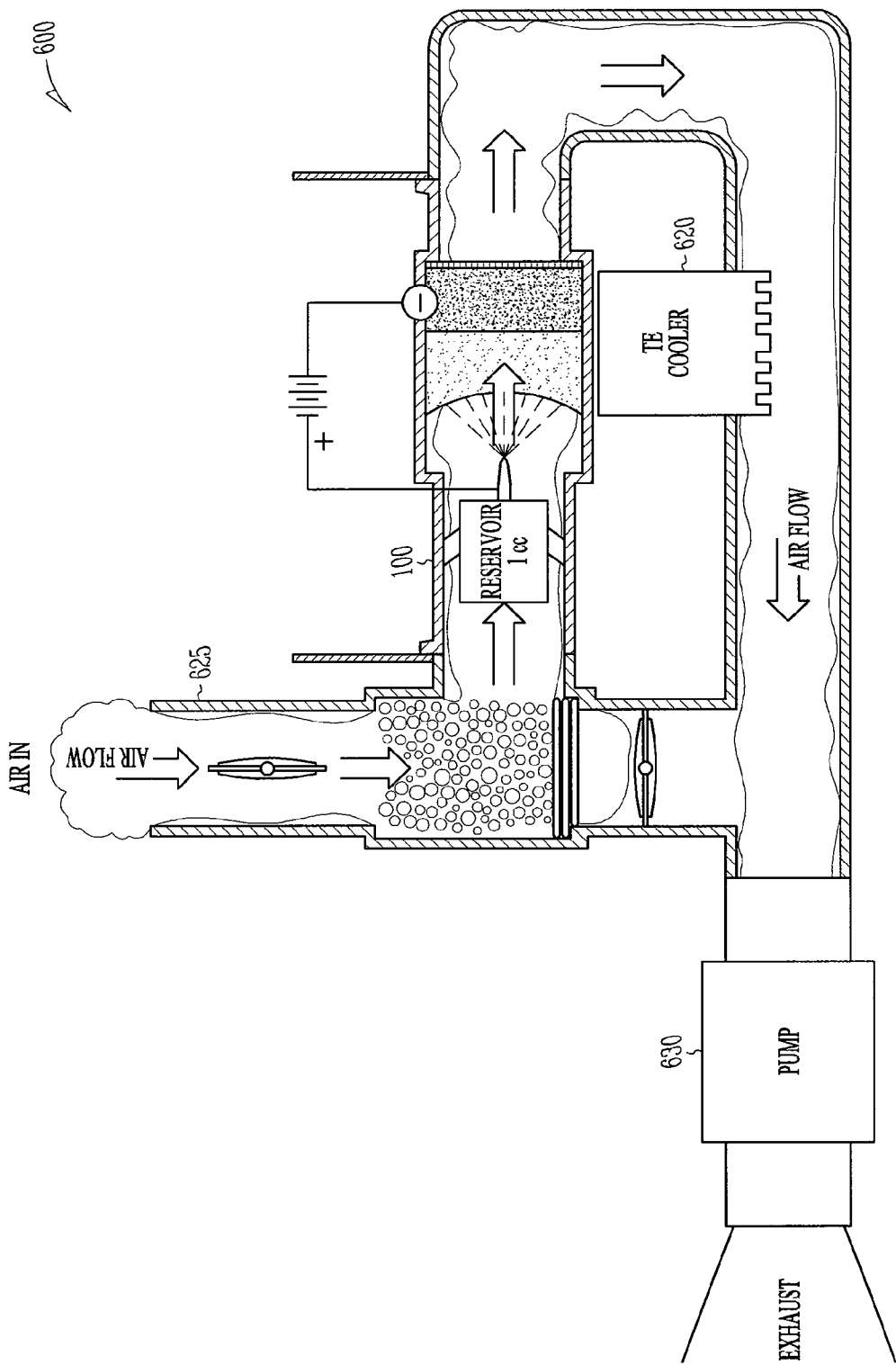
FIG. 6 is a block diagram of a system for sampling gas utilizing a gas sampling canister according to an example embodiment.

FIG. 6 is a block diagram of a system 600 for sampling gas utilizing a gas sampling canister 100 according to an example embodiment. The system includes a reusable air stream drying or water vapor removal module 610, a canister thermal management module 620, and an air pump/valves module 630. In one embodiment, the reusable water vapor removal module is positioned immediately downstream of a sample gas intake 635. One water selective absorbent or water scrubber is Zeolite 3 Å. The "3 Å" describes the 3 Angstrom pores sizes of this specialized Zeolite. The 3 Å pores do not adsorb any molecule larger than 3 Å. The molecules it will absorb are: helium, neon, nitrogen and water. They are commercially used for the dehydration of many liquids including ethanol, methane, and propylene. Their typical water removal efficiency is quoted as lowering water concentrations to approximately 1 ppm. If the system samples 5 L of air that is dried to 1 ppm $H_2O$. The ionic liquid absorbent will encounter 0.0040 mg of $H_2O$. In one embodiment, system 600 will nanospray approximately 0.3 ml or 525 mg of ionic liquid per sample. A fully functional Zeolite 3 Å drier may capture all of the water down to a 0.0008% (w/w) water to ionic liquid during one sampling cycle.

In one embodiment, approximately 10 g of Zeolite 3 Å may be used to adsorb all of the water that could be present in 5 L of 100% RH air sample. This amount of mass would be prohibitively large if it were included in each canister. The air stream drying module 635 in system 600 is designed to be reusable. Energy is provided for regenerating 10 g of Zeolite 3A between each sampling cycle in one embodiment. Taking typical value of Zeolite 3A specific heat of 1.07 kJ/kg. ° C. and ~250° C. regeneration temperature, ~2.5 kJ energy is used for one cycle of regeneration, which takes about 30 seconds in one embodiment. Primary lithium battery has a typical power density ~0.6 Watt.hr/g, it is estimated that ~1.2 g of battery is needed per sample.

Pneumatic pressure drop through the system is minimized, since the entire flow path, including the water removal module, the copper foam counter electrode, and the solid absorbent layer are highly porous. Air pumping at this low pressure can be readily achieved by either motion of a vehicle on which the system 600 is loaded, or a low power diaphragm gas pump. For example, a vehicle cruise at ~10 mph will provide 20 L/min air through a 1 $cm^2$ port.

However, larger air flow calls for higher power consumption. It is, therefore, highly desirable to have a system that offers high gas capturing efficiency. Less air sample that is used, means a lighter system. For example, a 19 L/min diaphragm pump weighs 17 lb (KNF Model UN813.5), compares to a 1.6 l/min pump that weighs merely 44 g (KNF Model NMPo15). In some embodiments, less than 5 L of actual air sample is needed, thus greatly reduces the weight of the overall system.

Cooling of the capturing counter electrode is provided for preservation of gases captured in the ionic liquid. The side effect is that it cools the air as well, which poses a power challenge for the overall system. In this system, a counter flow heat exchanger "recycles" the spent air to cool the hot side of a thermoelectrical cooler 620, hence reducing the power consumption of the overall system to <3 Watts in one embodiment.

Figure 7:
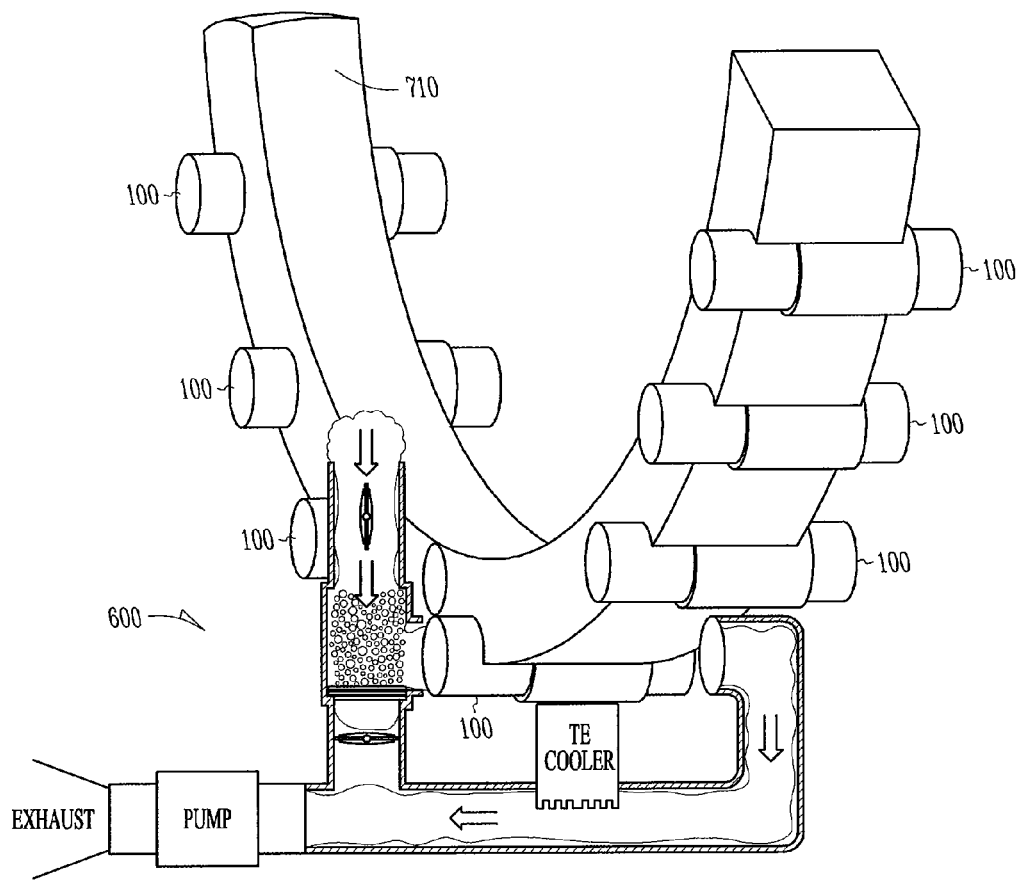
FIG. 7 is a perspective representation of a system for using multiple gas sampling cartridges to sample gas according to an example embodiment.

FIG. 7 is a perspective representation of a system 700 for providing multiple gas sampling cartridges to system 600 to sample gas according to an example embodiment. In system 700, multiple canisters 100 are provided on a circular frame 710 in one embodiment. One canister 100 is used for each cycle described above. In operation, a canister is delivered to the sampling system 600, the seals are opened, and air is flowed through the canister as described above. The canister is resealed, and placed back on the frame. The water remover is regenerated if needed, and the frame is moved to place the next canister into system 600 for another cycle. While a circular frame is illustrated, it is understood that many different canister handing devices may be used to deliver canisters to system 600 and remove them. As previously described, the used canisters may be sent to a laboratory for analysis.

CONCLUSION

Electrosprayed ionic liquids are used to capture chemicals in the atmosphere or gas sample. Electrosprayed ionic liquids offer several advantages for chemical capture compared to standard materials, such as Zeolites and activated carbons. Electrospray produces many small charged droplets. The droplets remain close to one another. The droplets effectively reduce the sampling time by increasing the surface area of the liquid and reducing mass transfer distances. A charge exists on the surface of the droplets and may electrostatically attract polar gas molecules. The use of ionic liquids for air sampling may also provide high capture capacity. Materials such as Zeolites and activated carbon have a finite number of adsorption sites, which limits the amount of molecules that can be captured. Adsorbing materials can become saturated in the presence of large background chemical signatures, and can potentially miss the presence of smaller amounts of chemicals because there are no adsorption sites left.

Once the chemicals are absorbed, the ionic liquids provide the ability to hold on to the adsorbed chemicals before future analysis. The adsorbed materials are prevented from evaporating by the relatively high freezing point and viscosity intrinsic to ionic liquids. Once solidified, any material not at the air-ionic liquid interface cannot evaporate. Ionic liquids have warmer freezing temperatures than traditional organic solvents. Furthermore, if the ionic liquid remain unfrozen, it remains a viscous liquid delaying the adsorbed material from reaching the gas-ionic liquid interface and thus delaying evaporation.

In one embodiment, a sampler system samples chemical analytes in air. A pump is used to draw in air to the sampler at a rate of up to 5 L/minute. The air that is sampled contains trace amounts of chemical analytes for capture. The air is first streamed over a water absorbing material, such as Zeolite 3A. Once the water content is removed, the air is directed into one of many interchangeable capture chambers. An individual capture chamber contains many components including: An electrospray nozzle with a reservoir of ionic liquid; a porous metal foam counter electrode with an exposed heat coupler; and a separate solid phase absorbing material. A new capture chamber may be used each time a different sample is collected. The air flow into a specific capture chamber is controlled by a series of valves.

Air streaming through the capture chamber flown through a plume of ionic liquid material that is generated by the electrospray nozzle. The chemical analytes in the air sample interact with the ionic liquid by first adsorbing on the droplet surface, then completely dissolving. The analyte-droplet combination is electrostatically driven towards a grounded porous metal foam that is thermoelectrically cooled. The analyte-droplet combination solidifies as they impact the cooled copper foam. The high surface area of the copper foam allows continuous capture of the ionic liquid droplets without clogging, permitting continuous air flow through the system.

Analytes that do not interact with the ionic liquids will not be captured on the metal foam, and will remain in the airflow. The remaining analytes will flow through a solid phase adsorbing material, such as activated carbon or Zeolite. Chemical analytes will interact with the solid phase material and adsorb to the surface. The air flowing out of the capture chamber is directed over a heat-sink attached to the thermoelectric cooler. The exhaust air is slightly chilled compared to ambient after interacting with the copper foam, and dissipates heat from the "hot side" of the cooler.

Less energy may be used to cool the copper foam because of the enhanced heat dissipation. The air-flow control valves operate to ensure that a small volume of air, typically on the order of 1 mL, remains in the capture chamber after the sampling cycle is over.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. An air sampling canister comprising:
   an electrospray nozzle for creating an ionic fluid electrospray plume;
   a gas sample intake positioned to provide a gas sample flowing through the ionic fluid electrospray plume;
   a water vapor removing module that removes water from an air flow and is coupled to the opening for the canister for providing the airflow to the ionic fluid electrospray; and
   a cooled counter electrode positioned to collect the electrospray plume such that selected chemicals in the gas sample are captured by ionic fluid accumulating on the cooled counter electrode.

2. The air sampling canister of claim 1 and further comprising:
   a reservoir for holding ionic fluid coupled to the electrospray nozzle.

3. The air sampling canister of claim 1 and further comprising a resealable seal on each end of the canister.

4. The air sampling canister of claim 3 wherein the canister is tubular in shape.

5. The air sampling canister of claim 1 wherein the cooled counter electrode comprises copper foam.

6. An air sampling canister comprising:
   an electrospray nozzle for creating an ionic fluid electrospray plume;
   a gas sample intake positioned to provide a gas sample flowing through the ionic fluid electrospray plume;
   a cooled counter electrode positioned to collect the electrospray plume such that selected chemicals in the gas sample are captured by ionic fluid accumulating on the cooled counter electrode; and
   a solid adsorbent downstream of the cooled counter electrode with respect to the flowing gas.

7. The air sampling canister of claim 6 wherein the solid adsorbent comprises activated carbon.

8. An air sampling system comprising:
   an opening for a canister having an ionic fluid electrospray nozzle and counter electrode;
   a cooler thermally coupled to the counter electrode;
   a water vapor removing module that removes water from an air flow and is coupled to the opening for the canister for providing the airflow to an ionic fluid electrospray.

9. The air sampling system of claim 8 wherein the water vapor removing module is rechargeable.

10. The air sampling system of claim 9 wherein the water vapor removing module comprises Zeolite.

11. The air sampling system of claim 8 wherein the cooler comprises a thermoelectric cooler.

12. The air sampling system of claim 11 wherein the cooler further comprises heat sink fins disposed in a return air path of air flowing through the canister.

13. The air sampling system of claim 8 and further comprising a pump for causing air samples to flow through the water vapor removing module and a canister when disposed in the canister opening.

14. The air sampling system of claim 8 and further comprising a rack for holding multiple canisters, wherein canisters are provided to the canister opening, is unsealed, air samples provided to the canister, the canister resealed, and returned to the rack.

15. A method of sampling air for chemicals, the method comprising:
   exposing an air sample to an ionic fluid electrospray plume;
   collecting nano droplets from the air sample exposed plume on a cooled surface proximate an electrospray counter electrode; and
   removing water vapor from the air sample prior to providing the air sample to the electrospray ionic plume.

16. The method of claim 15 wherein the droplets are collected as a gel on the cooled counter electrode.

17. The method of claim 16 wherein the cooled counter electrode is cooled to a temperature at least approximately 70 C below the temperature of the droplets.

18. The method of claim 15 and further comprising unsealing a canister that contains the ionic fluid electrospray plume and cooled counter electrode prior to exposing the air sample, and resealing the canister following exposing of the air sample.

19. The method of claim 18 and further comprising sequentially exposing multiple canisters in a canister rack to air samples.

* * * * *